United States Patent [19]
Brinkmann et al.

[11] Patent Number: 6,074,384
[45] Date of Patent: Jun. 13, 2000

[54] ENDOCARDIAL LASER REVASCULARIZATION WITH SINGLE LASER PULSES

[75] Inventors: Ralf E. W. Brinkmann, Luebeck; Heinrich Otto Teichmann, Bovenden; Peter Fuhrberg, Goettingen, all of Germany

[73] Assignee: PLC Medical Systems, Inc., Franklin, Mass.

[21] Appl. No.: 09/036,503

[22] Filed: Mar. 6, 1998

[51] Int. Cl.$^7$ .................................................. A61B 18/180
[52] U.S. Cl. ............................ 606/15; 606/10; 606/11; 606/12
[58] Field of Search .................. 606/2, 3, 14, 10, 606/11, 12, 9, 7, 15, 16, 17, 18, 19

[56] References Cited

U.S. PATENT DOCUMENTS

| | | | |
|---|---|---|---|
| 5,066,293 | 11/1991 | Furumoto | 606/9 |
| 5,125,926 | 6/1992 | Rudko et al. | 606/12 |
| 5,390,204 | 2/1995 | Yessik et al. | 606/12 |
| 5,662,644 | 9/1997 | Swor | 606/9 |
| 5,683,380 | 11/1997 | Eckhouse et al. | 606/10 |
| 5,832,013 | 11/1998 | Yessik et al. | 372/26 |
| 5,843,072 | 12/1998 | Furumoto et al. | 606/9 |
| 5,891,133 | 4/1999 | Murphy-Chutorian | 606/7 |
| 5,893,848 | 4/1999 | Negus et al. | 606/41 |

*Primary Examiner*—Linda C. M. Dvorak
*Assistant Examiner*—Sonya Harris-Ogugua
*Attorney, Agent, or Firm*—Fish & Richardson P.C.

[57] ABSTRACT

An apparatus for percutaneous laser revascularization of a patient's beating heart includes a laser system that produces a pulsed laser beam with a wavelength in a range of approximately 1.7 μm to approximately 2.15 μm, each pulse of the laser beam having a pulse duration in a range of approximately 1 ms and greater and having a pulse energy in a range of approximately 5 J to approximately 25 J. The pulse can include a train of micropulses. A fiber optic element that is coupled to the laser system is arranged with a catheter to pass through a vasculature of the patient and to deliver pulses of the laser beam to an interior wall of the patient's heart. The laser system can include a flash lamp-pumped laser in which a large capacitor bank discharges only a fraction of its stored energy through a flash lamp to fire the laser, wherein the capacitor discharge is turned off by a switchable device, such as a high current transistor, after the integrated energy of a laser pulse reaches a selected value. A pair of concave mirrors are arranged facing either end of the laser rod to form a resonant cavity, wherein each mirror has a curvature selected to compensate for changes in the index of refraction of the laser rod as a function of radius due to heating from the flash lamp. The laser system can be triggered to provide a laser pulse only during a refractive portion of the patient's heartbeat cycle. The apparatus is capable of forming a channel in the patient's heart to any desired depth by applying only a single laser pulse.

12 Claims, 5 Drawing Sheets

ENDOCARDIAL LASER REVASCULARIZATION WITH SINGLE LASER PULSES

BACKGROUND OF THE INVENTION

The invention relates to devices and methods for percutaneous endocardial revascularization of the heart using a flash lamp-pumped laser.

Transmyocardial revascularization (TMR) is a surgical treatment for cardiovascular disease. Present TMR procedure is an open chest technique (thoracotomy) that uses a laser beam to drill holes through the myocardium, typically into the left ventricle. These holes or channels extend through the entire heart wall thickness from the outside through to the ventricle. The openings of the channels on the outside surface of the heart heal due to external pressure from the surgeon, but the channels are believed to remain open on the inside, allowing blood to enter the heart wall tissue from the ventricle.

In another approach ELR can be performed using a catheter introduced percutaneously so that the tip of the catheter is inside a chamber of the heart, typically the left ventricle, where the holes or channels can be created from the inside toward but not through the outside of the heart. The channels are drilled with a laser beam introduced through the catheter.

Certain problems are presented when laser revascularization is done on a beating heart. A beating heart presents a moving target, which can make it difficult to accurately and consistently form channels of a desired depth and size. The heart also is extremely sensitive to a laser pulse at certain times during its cycle. A laser pulse striking the heart at the T time of an electrocardiogram (ECG) signal could cause the heart to fibrillate and result in heart failure. While one could stop the heart during the process of TMR, this poses other risks to the patient and complicates the operating procedure. The heart must be cooled and the patient connected to a heart-lung machine.

However, the risk of inducing a beating heart to fibrillate is greatly reduced when the laser is fired only during the refractory period of the heart cycle between the R and T waves of the ECG signal. An additional benefit of firing the laser only between the R and T waves is that this is the period of the heartbeat cycle during which the heart is most still and channels can be formed most accurately. Co-owned U.S. Pat. No. 5,125,926, to Rudko et al., describes a heart-synchronized pulsed laser system that fires a laser only during the refractory period of the heartbeat cycle. The '926 patent discloses an open chest procedure using an articulated optical arm or a fiber optic element to deliver the laser beam to the outer surface of the heart. The laser described in the '926 patent is a pulsed 50 Joule $CO_2$ laser, which produces a laser beam with a wavelength of about 10.6 $\mu$m. In a procedure using the articulated arm, a channel penetrating through the myocardium can be formed during a single firing of the laser, in a period of about 50 ms or less, during the refractory period of the heartbeat cycle.

U.S. Pat. No. 5,389,096, to Aita et al., discloses a percutaneous TMLR procedure in which a steerable heart catheter is guided from the femoral artery via the abdominal artery into the left ventricle. The laser energy is delivered through the working channel of the catheter by a fiber optic delivery system. The '096 patent describes a system employing a holmium laser, which produces a beam having a wavelength of about 2.1 $\mu$m. This wavelength is desirable for TMLR because it is strongly absorbed by heart tissue, and so is efficient for forming channels. It is also a wavelength that can be passed through a fiber optic element.

Presently available flash lamp-pumped lasers typically include a capacitor bank that discharges through a thyristor to energize a flash lamp. The capacitor bank, which typically stores a couple of hundred Joules of energy and has a capacitance of a couple hundred $\mu$f, completely discharges when the thyristor is enabled. The flash lamp only flashes during the discharge. This typically takes no more than a few hundred microseconds ($\mu$s). Because the laser is pumped only during the operation of the flash lamp, the laser beam produced by the laser rod in the prior art systems is also limited to a pulse duration of only a few hundred $\mu$s. Moreover, prior art flash-pumped holmium lasers used for ELR could only produce pulses with a maximum energy of about 3–5 Joules (J) at a power of about 10 KW.

The energy necessary to form a 10 mm channel in the heart, which is a desirable depth for revascularization, is typically greater than 5 J, for example, 10–20 J. However, due to limitations of the optical coatings of components in the laser cavity, these short pulses, having a duration of a few hundred $\mu$s, cannot be generated with much higher energies without damaging the laser. Therefore, as described in the '096 patent, several lower energy pulses applied at a frequency of at least 2 Hz are required to form each channel, the pulses being applied over the course of more than one heartbeat. The '096 patent also describes employing an excimer laser. However, an even greater number of laser pulses are needed with the excimer laser, again due to limitations of the fiber optic system.

A variety of problems arise when more than one pulse is employed to form a channel through the heart wall. After each laser pulse, the channel being formed can fill with blood, which absorbs much of the energy of subsequent pulses, making the subsequent pulses less efficient in deepening the channel. A beating heart can also move between pulses, and the surgeon must be particularly careful to direct the laser beam of each pulse along the same line. If the laser pulses are applied during different heartbeats, these problems can be multiplied. Moreover, due to the cavitation effects during ablation, a high risk of catheter displacement from the endocardium is presented.

SUMMARY OF THE INVENTION

The invention provides an apparatus for percutaneous laser revascularization, or endocardial laser revascularization (ELR), of a patient's beating heart. The apparatus includes a laser system structured and arranged to produce a pulsed laser beam with a wavelength in a range of approximately 1.7 $\mu$m to approximately 2.2 $\mu$m, each pulse of the laser beam having an overall duration in a range of approximately 0.1 ms or greater and having a pulse energy in a range of approximately 5 J to approximately 25 J. In another device, this pulse may include a burst of several micropulses in order to optimize ablation. The apparatus also includes a laser pulse delivery system, including a fiber optic element coupled to the laser system. The fiber optic element is arranged with a catheter that is structured and arranged to pass through a vasculature of the patient to deliver pulses of the laser beam to an interior wall of the patient's heart. The laser system can be switched to provide a laser pulse only during a refractive portion of the patient's heartbeat cycle. The apparatus is capable of forming a channel in the patient's heart to a depth of approximately 10 mm or more by applying only a single long laser pulse as described above.

According to one aspect of the invention, a laser system that can be used with the apparatus for percutaneous laser revascularization includes a flash lamp-pumped laser. The laser includes one or more flash lamps arranged in proximity to a laser rod for activating the laser rod to lase when the flash lamps are turned on. For each flash lamp, a high capacity capacitor bank stores energy for driving the flash lamp. Each capacitor bank stores about 3000 Joules or more. In one embodiment, each capacitor bank has a capacitance of about 62 millifarrads (mF) and is used in conjunction with a 600 V DC power supply. A switchable device, such as a high current transistor, is connected in series with each capacitor bank and associated flash lamp, the device being responsive to a close circuit control signal to switch from a normally open circuit configuration to a closed circuit configuration to turn on the flash lamp, and being responsive to an open circuit control signal when a current is passing through the switchable device to switch from the closed circuit configuration to the open circuit configuration to turn off the flash lamp. The laser system also includes a controller producing the close circuit and open circuit control signals.

The laser system can further include an energy detector structured and arranged to produce a power signal indicative of the power of a laser beam pulse produced by the flash-pumped laser, wherein the controller determines an integrated pulse energy of the laser beam pulse in response to the power signal and provides the open circuit control signal to turn off the laser pulse or train of micropulses when the integrated pulse energy reaches a selected energy.

The switchable device can include a first high current transistor arranged in series between the capacitor bank and a first terminal of the flash lamp, and a second high current transistor arranged in series between a second terminal of the flash lamp and ground, each of the transistors being responsive to the open circuit and the close circuit control signals. The switchable device can further include a resistor having a high resistance also being connected between the second terminal and ground, and a simmer voltage supply being connected to the first terminal and providing a small current through the flash lamp and the resistor such that the flash lamp is kept conducting when the transistors are open circuit. This enables the flash lamp respond very quickly, in a time period of less than about 1 $\mu$s, to the transistors switching from open circuit to closed circuit.

With this system, a single long laser pulse with a duration of more than about 1 ms can be produced for ELR, without completely discharging the capacitor bank. Alternatively, the controller can rapidly switch the switchable device associated with each flash lamp, back and forth, between open circuit and closed circuit to produce a train of closely spaced short duration micropulses, wherein the train of micropulses has a duration of greater than about 1 ms and the capacitor bank is only partially discharged with each of the micropulses. A revascularization channel having any desired depth can be formed with a single long pulse or a single train of micropulses during the refractory period of a single heartbeat.

According to yet another aspect of the invention, the flash lamp-pumped laser system includes a pair of concave curvature mirrors arranged facing either end of the laser rod to form a resonant cavity, wherein each mirror has a curvature selected to compensate for changes in the index of refraction of the laser rod as a function of radius when the laser is operated. The change in the index of refraction is due to the inhomogeneuous heating of the outer portion of the laser rod by the flash lamps over the duration of each long pulse or train of micropulses. The mirror curvature can be spherical, with a radius of about 1 m.

In each of the above-described systems, the laser can be, for example, a holmium (Cr:Tm:Ho:YAG) laser producing light at a wavelength of about 2.123 $\mu$m or a thulium (Cr:Tm:YAG) laser producing light at a wavelength of about 2.01 $\mu$m. YAP type lasers can also be employed. The wavelength of light produced by laser rods of this type can be altered by changing the doping of the laser rod and by introducing wavelength selecting elements into the path of the optical resonator. Any wavelength around the water absorption peat of about 1.94 typically between 1.7 and 2.2 $\mu$m is reasonable for ELR The ELR described herein follows the proved single pulse application method of $CO_2$ laser-TMLR, up to now the only system which demonstrated clinical success. An advantage of the invention is that it provides an improved procedure for laser revascularization of the heart with regard to minimal invasive surgery by means of steerable heart catheter in a percutaneous approach. However, the laser system of this invention can also be employed in a thoracic TMLR procedure.

The laser system of the present apparatus provides a laser beam with a wavelength that is strongly absorbed in heart muscle. The percutaneous laser revascularization system can form a complete channel to a desired depth with a single laser pulse or single train of micropulses having a duration of up to about 50 ms. Employing a single long duration pulse or train of micropulses in the refractory period of a single heartbeat allows the channel to be formed without filling with blood or otherwise becoming blocked off during the channel forming process, as can happen with multi-pulse methods wherein the pulses are widely spaced apart and applied over the course of more than one heartbeat. The risk that the heart will move or the catheter tip displaced aduring the channel forming process is greatly reduced by forming a complete channel during a single heartbeat with a single pulse in the refractive period of the heartbeat cycle.

The flash lamp-pumped laser of his invention can provide pulses of much greater duration and energy than previously available with lasers suitable for percutaneous ELR. These long duration and higher energy pulses can be coupled to optic fiber elements without damaging the optic fibers because the energy is transmitted over a longer period of time, reducing the power load on the optic fibers.

DETAILED DESCRIPTION OF THE INVENTION

Figure 1:
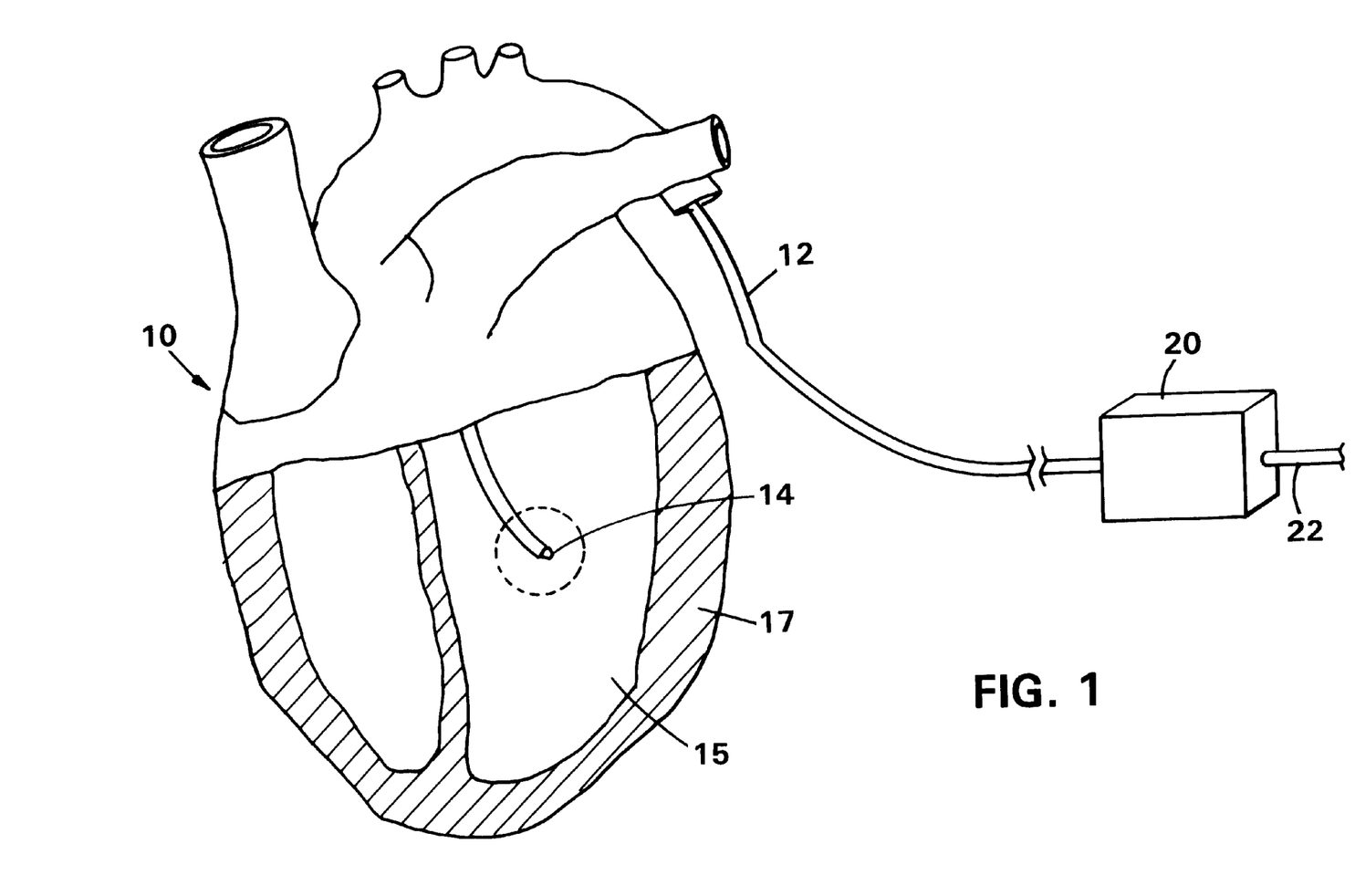
FIG. 1 is partially sectioned perspective view of a heart catheter disposed with its tip located in a chamber of the heart FIG. 2. is a block diagram of an ELR laser system according to the invention.

Referring to FIG. 1, a steerable catheter 12 according to this invention is inserted through the aorta with a tip 14 at its distal end located within a chamber of a human heart 10, typically the left ventricle. Tip 14 is immersed in blood 15 and is shown approaching a wall 17 of the left ventricle. A proximal end of catheter 12 includes a housing 20 into which a fiber optic element 22 enters. Fiber optic element 22 passes through catheter 12 to distal tip 14. As described below, distal tip 14 includes an sapphire element 24 (see FIG. 2) arranged to collimate light energy from fiber optic element 22 into a beam to form channels in heart wall 17. Fiber optic element 22 includes a 400 μm, low OH optic fiber that is optimized for low losses, and which may be obtained from 3M Co. of Minneapolis, Minn. Catheter 12 is 8–9 French.

Housing may also include ultrasonic circuit 26 coupling to a transducer and ultrasonic detector (not shown) at distal tip 14 for measuring the thickness of heart wall 17 and/or monitoring the depth of a channel as it is formed in heart wall 17. An ultrasonic detection system is described in detail in co-owned U.S. patent application No. Ser. 08/735,658, to Negus et al., the entire disclose of which is incorporated herein by reference, and in International patent application Ser. No. PCT/US97/19036, to Negus et al., published April, 1998.

Figure 2:
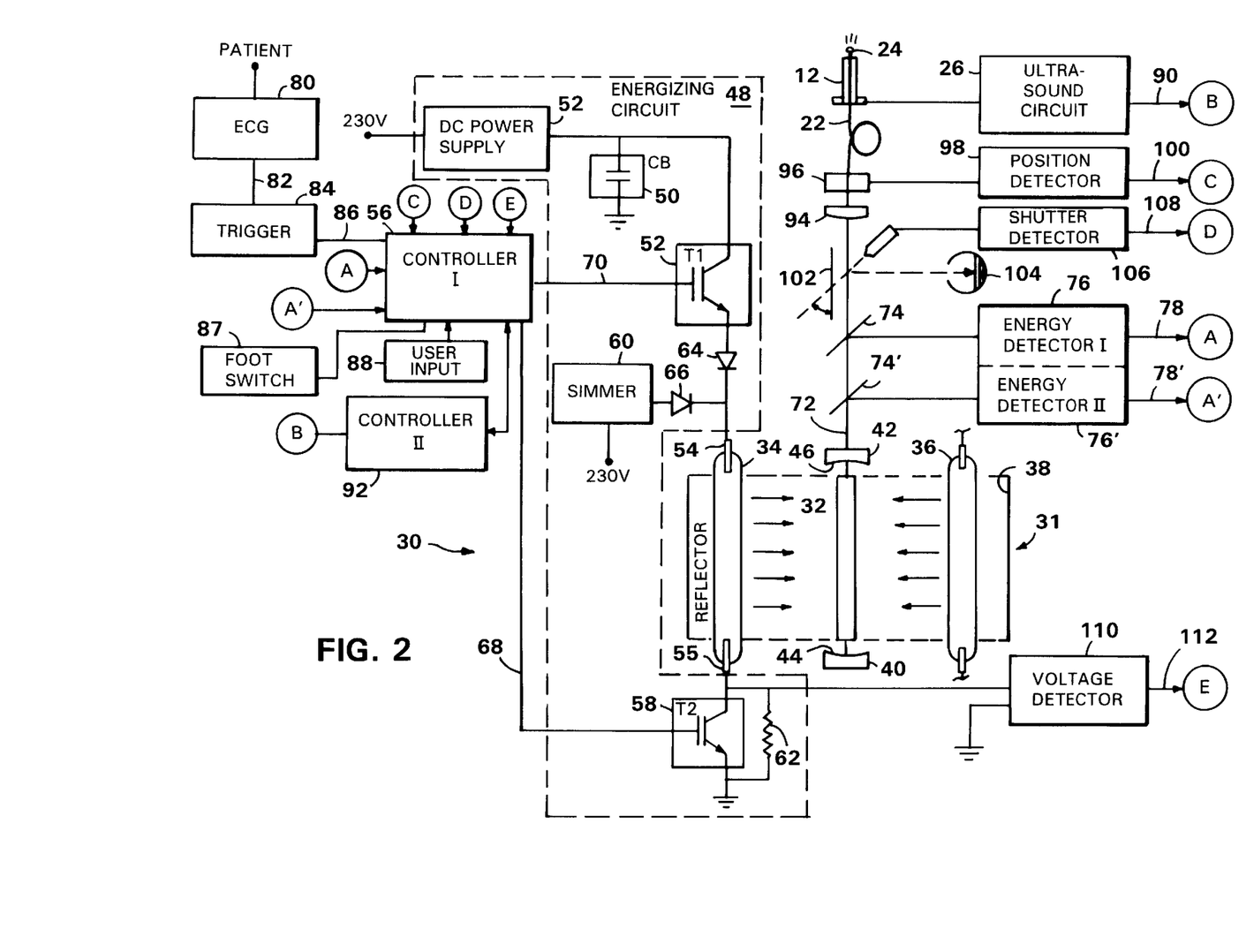

Referring now also to FIG. 2, fiber optic element 22 is coupled to a flash lamp-pumped laser system 30. Laser system 30 is capable of producing single pulses of laser light at a wavelength of about 1.7 μm to about 2.15 μm, each pulse having a pulse duration of between about 1 ms and 20 ms, and having a pulse energy of between about 5 and 25 J. Each pulse, when coupled through fiber optic element 22, is capable of forming a channel in heart wall 17 during the refractive period of the heartbeat cycle. As will be described in detail below, laser system 30 includes means for forming a channel to a desired depth with a long duration pulse or train of micropulses.

Laser system 30 includes a flash lamp-pumped laser 31 having a laser rod 32, which can be, for example, a holmium (Cr:Tm:Ho:YAG or Cr:Tm:Ho:YAP) rod or a thulium (Cr:Tm:Ho:YAG or Cr:Tm:YAP) rod. A holmium laser rod can provide a laser beam with a wavelength of about 2.123 μm, and a thulium laser rod can provide a laser beam with a wavelength of about 2.01 μm, which is about 2.6 times more strongly absorbed by tissue than light at 2.123 μm. Laser rod 32 has a diameter of about 6.3 mm and a length of about 125 mm. Laser rods meeting these specification can be obtained from Union Carbide Corporation.

Two flash lamps 34, 36 are arrayed on either side of laser rod 32. Although the described embodiment employs two flash lamps, laser 31 could be configured with a single flash lamp or more than two flash lamps. Flash lamps 34, 36 have a bore diameter of about 5 mm, an arc length of about 100 mm, and are filled with xenon to a pressure of about 450 Torr. A ceramic reflector 38 substantially surrounds laser rod 32 and flash lamps 34, 36.

A pair of mirrors 40, 42, spaced about 300 mm apart, are arranged facing the ends of laser rod 32 to form a laser cavity. Mirror 40 is highly reflective. Mirror 42 is partially reflective, having a transmittance of about 20%, and includes an anti-reflective coating on its backside. Mirrors 40, 42 have spherical concave reflecting surfaces 44, 46, respectively, which have a radius of curvature of about 1 m.

Flash lamps 34, 36 are energized by separate energizing circuits, each having a dedicated capacitor bank (CB). Only energizing circuit 48, which is coupled to flash lamp 34, is shown in FIG. 2, but it will be understood that flash lamp 36 is coupled to a separate, but identical energizing circuit. Energizing circuit 48 includes a 62 mF CB 50, available from Panasonic Corporation, that is charged by a 600 V DC power supply 52, by which CB 50 can store about 11,000 J. The stored energy E of each capacitor bank, which should be at least about 3000 J, can be adjusted by changing the voltage and/or the capacitance according to $E=\frac{1}{2}CV^2$. A high power transistor (T1) 52, which is available from Eupec in Germany, is connected in series between CB 50 and a terminal 54 at one end of flash lamp 34. A terminal 55 at the other end of flash lamp 34 is coupled to ground through a second high power transistor (T2) 58, which is identical to T1 52.

Switching of both T1 52 and T2 53 is controlled by controller I 56 as will be described in greater detail below. Both T1 52 and T2 54 are normally open circuit. Because flash lamps do not ignite at voltages of several hundred volts, a high voltage, current controlled power supply (simmer) 60 is used to keep flash lamp 34 continuously conductive with a low current discharge of about 60–100 mA. This enables flash lamp 34 to be turned on within a very short time period, on the order of about 0.5 μs. The simmer current passes to ground through a resistor 62, which has a resistance of about a few hundred KΩ. Blocking diodes 64, 66 protect T1 52 and simmer 60, respectively.

CB 50 has a much higher capacitance, about 62 mF, a lower voltage, about 600–700 V, and a much greater stored energy, about 11,000 J, when fully charged than previous flash lamp-pumped holmium laser systems used for percutaneous TMR. The higher capacitance, lower voltage and higher stored energy of CB 50 in combination with the characteristics of the xenon flash lamp 34, allow flash lamp 34 to operate for a duration of 0.1 ms up to about 10 ms or more, which in turn causes laser rod 32 to produce a laser beam with a pulse duration of up to about 10 ms or more. Longer pulses can be obtained by storing more energy in CB 50. For ELR carried out only during a refractory period of the heart cycle, the pulse duration can be up to about 50 ms. Only a fraction of the energy stored in CB 50, about 5% to about 50%, is actually used to produce a laser pulse with a 10 ms duration. Increasing the laser pulse duration permits the use of much higher energy laser pulses with a lower power output than previously obtainable with lasers of this type. For example, the described system can produce a laser pulse 72 with a pulse duration of about 8–10 ms and a pulse energy of about 16–20 J at a power of about 2 KW using a holmium laser rod. Only about 10% of the energy stored in CB 50 is used to produce such a pulse.

Flash lamp 34, which can operate for up to about 50 ms, can heat the outer portion of laser rod 32 such that laser rod 32 has an index of refraction that varies with radius. The non-uniform index of refraction can defocus laser pulse 72. The curvature of mirror surfaces 44, 46 is selected to compensate for the defocusing.

As mentioned above, both T1 52 and T2 58 are normally in an open circuit configuration. To initiate laser pulse 72, controller I first provides a close circuit control signal on line 68 that switches T2 58 to a closed circuit configuration. After about 1 ms, controller I 56 provides a close circuit control signal on line 70 that switches T1 52 to a closed circuit configuration. CB 50 then discharges through flash lamp 34, pumping laser rod 32, and thereby producing laser pulse 72. To end laser pulse 72, controller I 56 produces an open circuit control signal first to T1 52 on line 70, and then another open circuit control signal to T2 5 on line 68. This shuts off flash lamp 34 and in turn causes laser rod 32 to stop producing laser pulse 72.

Laser pulse 72 is coupled to optic fiber element 22 through a sapphire focusing lens 94. A proximal end of fiber optic element 22 is in a mounting 96, which includes an optical connector, at a fixed position relative to lens 94. A position detector 98 coupled to mounting 96 provides a position error signal 100 to controller I 56 if the optial axis of the fiber optic connector is not in the proper position. Controller I 56 will not allow laser 31 to operate if there is a misalignment.

System 30 is adapted to produce laser pulse 72 only during the refractive period of a patient's heartbeat cycle. A heart-synchronized system for providing a pulsed laser beam only during the refractive period of the heartbeat is described in detail in U.S. Pat. No. 5,125,926, to Rudko et al., the entire disclosure of which is included herein by reference. It suffices for this description to mention that the patient's heartbeat is monitored with an ECG 80, which produces an ECG signal 82 indicative of the heartbeat cycle. A trigger circuit 84 responsive to the ECG signal 82 determines a safe time of the heartbeat cycle in which to fire laser 31, and provides a trigger signal 86 to controller I 56. In response, controller I 56 provides the close circuit control signals to T2 58 and T1 52, which causes laser 31 to produce laser beam pulse 72. A foot switch 87 or any other type of switch easily operated by the surgeon is used to enable trigger signal 86. Laser system 30 delivers laser pulse 72 only when the foot switch 87 is depressed and when trigger 84 provides trigger signal 86. Only one laser pulse 72 is provided for each depression of foot switch 87. A foot switch system is described in U.S. Pat. No. 5,125,926. The surgeon would close and open foot switch 87 to form each channel. The electronics of trigger 84 could be incorporated into controller I 56.

An important feature of the invention is that the power of a laser pulse 72 produced by laser 31 is measured, and laser 31 is switched off when the integrated energy of laser pulse 72 reaches a selected energy. A redundant system includes a pair of beam splitters 74, 74' that each direct a fraction of laser beam 72 energy to respective energy detectors 76, 76', which each include an InGaAs photodiode detector. Energy detectors 76, 76' provide respective power signals 78, 78' indicative of the power of laser pulse 72 to controller I 56. Controller I determines an integrated energy of laser pulse 72 based on power signals 78, 78'. Controller I 56 includes a user input 88 for inputting a selected pulse energy. When the integrated energy reaches the selected pulse energy, controller I 56 provides the open circuit control signals to T1 52 and to T2 58 to shut down laser 31.

Ultrasound circuit 26 can also be used to set the selected energy. Similar to the system described in U.S. patent application Ser. No. 08/735,658, ultrasound circuit 26 can provide an ultrasound signal 90 to controller II 92. Controller II 92 determines a thickness of heart wall 17 based on the ultrasound signal and provides a thickness signal indicative the heart wall thickness. One or the other of controller I 56 and controller II 92 determines the selected energy based upon the thickness signal before beginning to form a channel in heart wall 17 with laser pulse 72. The selected energy is chosen such that laser pulse 72 forms a channel that does not penetrate completely through heart wall 17. For example, a channel depth that is about 80% of the thickness of heart wall 17 provides effective revascularization.

Ultrasound circuit 26 can also provide a first ultrasound signal 90 prior to applying a laser beam pulse to the interior wall, and controller II 92 can provide a first thickness signal indicative of the thickness of heart wall 17 in response to ultrasound signal 90. Then, during the process of forming a channel in heart wall 17 with laser pulse 72, ultrasound circuit 26 can provide additional ultrasound signals 90 and controller II 92 can provide a additional thickness signals indicative of a depth of a channel being formed by laser pulse 72 in heart wall 17. Either controller II 92 or controller I 56 then makes a comparison of the first thickness signal and subsequent thickness signals, and provides a signal to terminate laser pulse 72 when the channel reaches a depth that is a selected fraction of the thickness indicated by the first thickness signal. Controller I 56 then provides the open circuit control signals to T1 52 and T2 58 in response to terminate signal.

It will be understood that the functions ascribed to controller I 56 and controller II could be combined in a single controller unit. Controller I 56 and controller II 92 each include a microprocessor, such as, for example a V25 processor produced by NEC. To comply with directives for medical devices in some countries, neither controller employs DRAM devices, but instead uses static RAM devices. Methods for making controllers for signal processing process control are well known, and the above-described functions of controller I 56 and controller II 92 can be realized in a variety of configurations.

A movable mirrored shutter 102 can be operated to direct laser pulse 72 to a beam stop 104. Shutter 102 should be opened to allow laser pulse 72 to couple to fiber optic element 22 only when the surgeon is ready to form a channel. Shutter 102 can be controlled, for example, with foot switch 87, or another surgeon controlled switch. A shutter detector 106 provides a shutter error signal 108 to controller I 56 if shutter 102 is improperly positioned. Controller I 56 also will not allow laser 31 to operate in response to a shutter error signal.

Laser system 30 also includes a voltage detector 110 measuring a voltage across resistor 62. This provides an indication of whether T2 58 is in an open circuit or a closed circuit configuration, or whether T2 58 is malfunctioning. Voltage detector 110 provides a signal 112 indicative of the voltage across resistor 62. Controller I 56 will shut down laser 31 if signal 112 indicates an error condition.

Laser pulse 72 for forming a channel in heart wall 17 can be a single pulse of a selected energy or a train of closely spaced micropulses having, in total, the selected energy. In both cases, laser pulse 72 only partially discharges CB 50.

Figure 3:
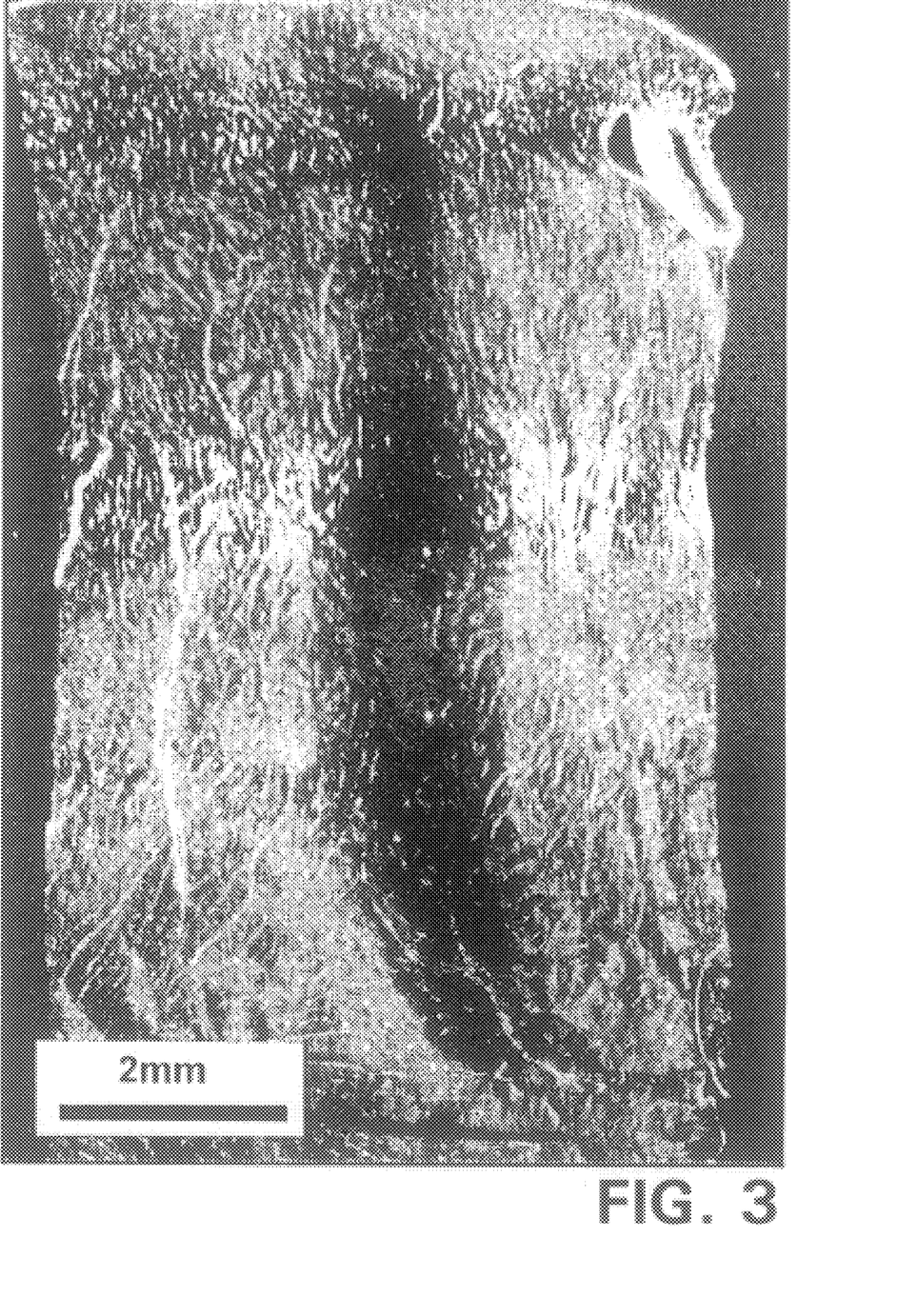
FIGS. 3 and 4 are photographs of sections of channels formed in myocardial tissue employing single $CO_2$ and holmium laser pulses, respectively.
Figure 4:
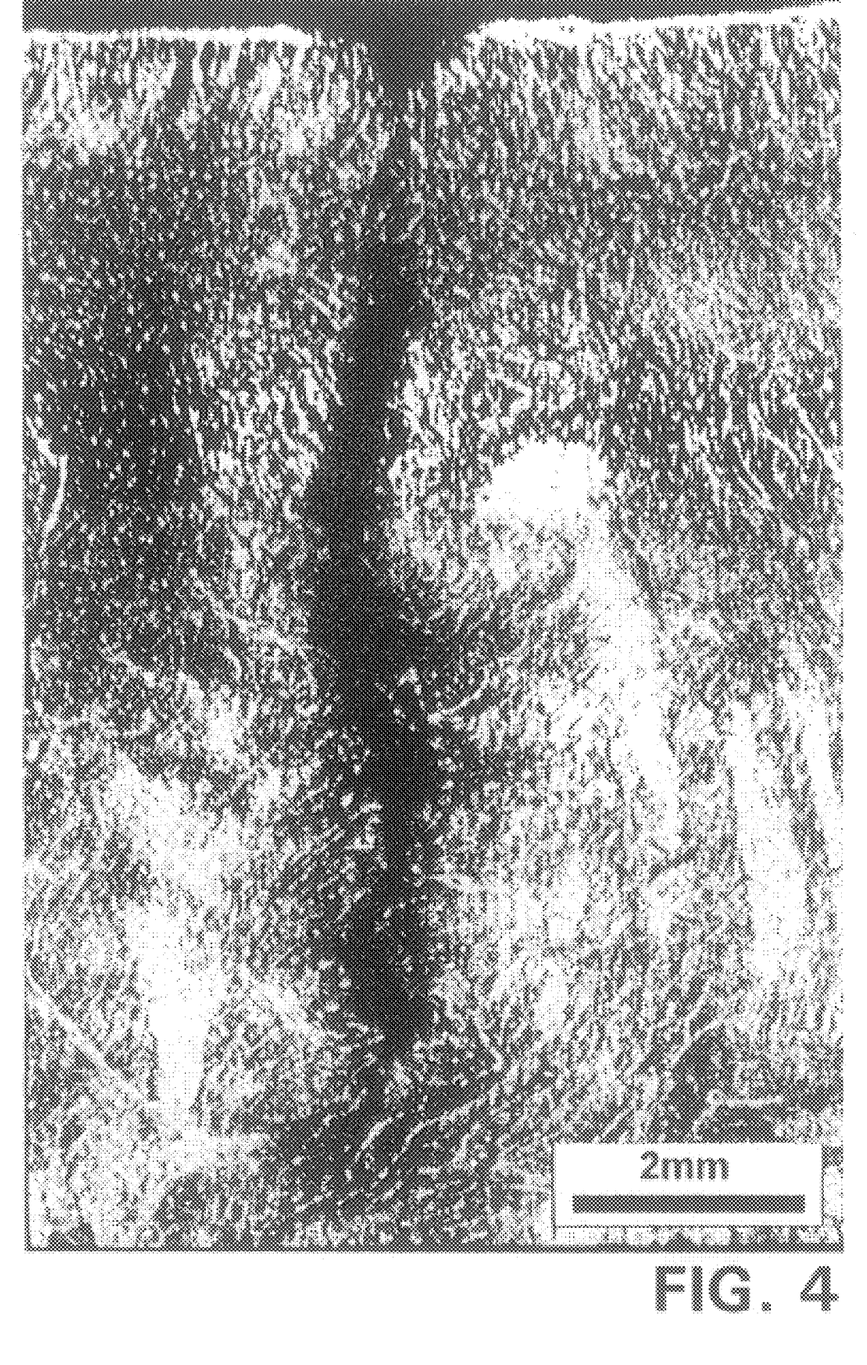

We demonstrated a suitable concept for endocardial laser revascularization (ELR) with single high energy holmium laser pulses. Pulses with energies of up to 12 J transmitted by 400 $\mu$m core diameter fibers were directed to an ex vivo, beating porcine heart perfused with blood. We found that these pulse energies are sufficient to ablate myocardial channels of up to 10 mm in length. We compared our results with channels formed on the porcine model with an 800 W $CO_2$ laser. The tissue ablation rates are nearly identical for the holmium and $CO_2$ laser. FIGS. 3 and 4 illustrate channels formed using 10 J pulses produced by the holmium laser and the $CO_2$ laser, respectively. The pulse duration for the holmium laser pulses was 4 ms.

Figure 5:
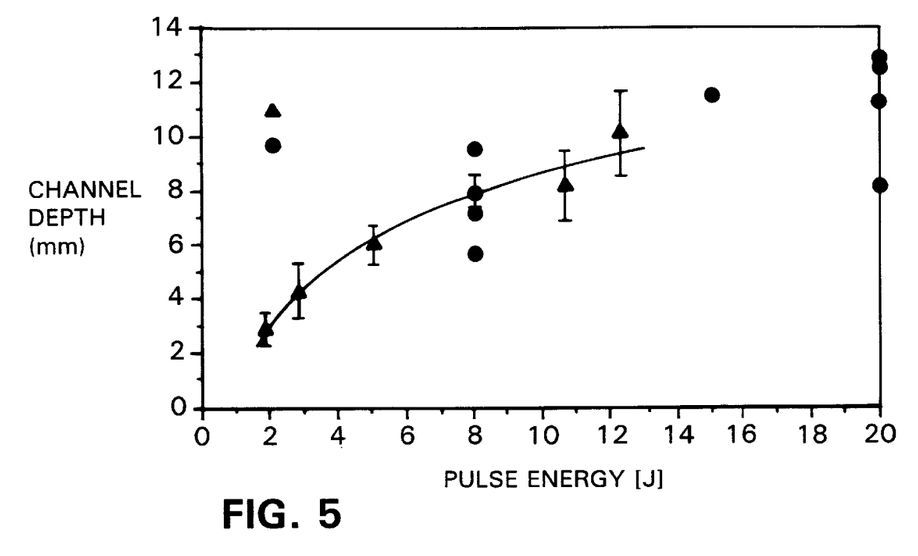
FIG. 5 is a plot of a channel depth as a function of the energy of single holmium and $CO_2$ laser pulses.

FIG. 5 shows the channel depth as a function of the energy of single holmium and $CO_2$ laser pulses. Exceeding the ablation threshold the channel depths increase nearly logarithmically with energy for both laser systems. In the case of the holmium laser each point is the mean of to lesions, with the standard deviation being shown. For the $CO_2$ laser channels the number of measurements performed were too low for statistical evaluation, so single events are plotted. In the energy range of 2 to 20 J being investigated, the ablation rates of the two laser systems are quite similar.

Other embodiments are within the scope of the following claims.

What is claimed is:

1. An apparatus for percutaneous laser revascularization of a patient's heart, comprising:

a laser system structured and arranged to produce a pulsed laser beam, each pulse of the laser beam having a pulse duration in a range of approximately 1 ms and greater;

a laser pulse delivery system, including a fiber optic element arranged to transmit the pulsed laser beam, the fiber optic element being arranged with a catheter that is structured and arranged to pass through a vasculature of the patient to deliver pulses of the laser beam to an interior wall of the patient's heart, further comprising a controller that selects the energy delivered by said pulsed laser beam, and sensing means for providing a first thickness signal indicative of a thickness of the interior wall of the patient's heart, wherein the controller determines the selected energy based upon the thickness signal.

2. The apparatus of claim 1, wherein the laser system comprises:

a flash-pumped laser, including a laser rod and a flash lamp arranged in proximity to the laser rod for causing the laser rod to lase when the flash lamp is turned on;

a capacitor storing energy;

a switchable device connected in series with the capacitor and the flash lamp, the switchable device being responsive to a close circuit control signal to switch from a normally open circuit configuration to a closed circuit configuration to turn on the flash lamp, and being responsive to an open circuit control signal to switch, when a current is passing through the switchable device, from the closed circuit configuration to the open circuit configuration to turn off the flash lamp; and said controller producing the close circuit and open circuit control signals.

3. The apparatus system of claim 2, further comprising an energy detector structured and arranged to produce a power signal indicative of the power of each laser beam pulse produced by the flash-pumped laser, wherein the controller determines an integrated pulse energy of each laser beam pulse in response to the power signal and provides the open circuit control signal when the integrated pulse energy of each laser beam pulse reaches a selected energy.

4. The apparatus system of claim 2, wherein the switchable device comprises a high current transistor, and wherein the laser rod comprises one of a holmium laser rod and a thulium laser rod.

5. The apparatus of claim 2, wherein the flash-pumped laser further includes a pair of concave mirrors arranged facing either end of the laser rod to form a resonant cavity, wherein each mirror has a curvature selected to compensate for changes in the index of refraction of the laser rod as a function of radius when the laser is operated.

6. The apparatus of claim 5, wherein the curvature of each mirror is a spherical curvature.

7. The laser system of claim 2, wherein the capacitor stores an energy of at least about 3000 J.

8. The laser system of claim 2, wherein the switchable device may be operated such that the pulse comprises a train of micropulses.

9. An apparatus for percutaneous laser revascularization of a patient's heart, comprising:

a laser system structured and arranged to produce a pulsed laser beam with a wavelength in a range of approximately 1.7 $\mu$m to approximately 2.15 $\mu$m, each pulse of the laser beam having a pulse duration in a range of approximately 1 ms and greater and having a pulse energy in a range of approximately 5 J to approximately 25 J;

a laser pulse delivery system, including a fiber optic element arranged to transmit the pulsed laser beam, the fiber optic element being arranged with a catheter that is structured and arranged to pass through a vasculature of the patient to deliver pulses of the laser beam to an interior wall of the patient's heart, wherein the laser system comprises:

a flash-pumped laser, including a laser rod and a flash lamp arranged in proximity to the laser rod for causing the laser rod to lase when the flash lamp is turned on;

a capacitor storing energy;

a switchable device connected in series with the capacitor and the flash lamp, the switchable device being responsive to a close circuit control signal to switch from a normally open circuit configuration to a closed circuit configuration to turn on the flash lamp, and being responsive to an open circuit control signal to switch, when a current is passing through the switchable device, from the closed circuit configuration to the open circuit configuration to turn off the flash lamp; and a controller producing the close circuit and open circuit control signals, further comprising an energy detector strictured and arranged to produce a power signal indicative of the power of each laser beam pulse produced by the flash-pumped laser, wherein the controller determines an integrated pulse energy of each laser beam pulse in response to the power signal and provides the open circuit control signal when the integrated pulse energy of each laser beam pulse reaches a selected energy, further comprising sensing means for providing a first thickness signal indicative of a thickness of the interior wall of the patient's heart, wherein the controller determines the selected energy based upon the thickness signal.

10. An apparatus for percutaneous laser revascularization of a patient's heart, comprising:

a laser system structured and arranged to produce a pulsed laser beam with a wavelength in a range of approximately 1.7 $\mu$m to approximately 2.15 $\mu$m, each pulse of the laser beam having a pulse duration in a range of approximately 1 ms and greater and having a pulse energy in a range of approximately 5 J to approximately 25 J;

a laser pulse delivery system, including a fiber optic element arranged to transmit the pulsed laser beam, the fiber optic element being arranged with a catheter that is structured and arranged to pass through a vasculature of the patient to deliver pulses of the laser beam to an interior wall of the patient's heart, wherein the laser system comprises:

a flash-pumped laser, including a laser rod and a flash lamp arranged in proximity to the laser rod for causing the laser rod to lase when the flash lamp is turned on;

a capacitor storing energy;

a switchable device connected in series with the capacitor and the flash lamp, the switchable device being responsive to a close circuit control signal to switch from a normally open circuit configuration to a closed circuit configuration to turn on the flash lamp, and being responsive to an open circuit control signal to switch, when a current is passing through the switchable device, from the closed circuit configuration to the open circuit configuration to turn off the flash lamp; and a controller producing the close circuit and open circuit control signals, further comprising an energy detector structured and arranged to produce a power signal indicative of the power of each laser beam pulse produced by the flash-pumped laser, wherein the controller determines an integrated pulse energy of each laser beam pulse in response to the power signal and provides the open circuit control signal when the integrated pulse energy of each laser beam pulse reaches a selected energy, further comprising sensing means for providing the controller a first thickness signal indicative of a thickness of the interior wall of the patient's heart prior to applying a laser beam pulse to the interior wall, and providing a second thickness signal indicative of a depth of a channel being formed in the interior wall of the patient's heart by one of the laser beam pulses, and wherein the controller provides the open circuit control signal when the second thickness signal indicates a depth that is a selected fraction of the thickness indicated by the first thickness signal.

11. An apparatus for percutaneous laser revascularization of a patient's heart, comprising:

a laser system structured and arranged to produce a pulsed laser beam, each pulse of the laser beam comprising a series of micropulses, the series having a duration in a range of approximately 1 ms and greater;

a laser pulse delivery system, including a fiber optic element arranged to transmit the pulsed laser beam, the fiber optic element being arranged with a catheter that is structured and arranged to pass through a vasculature of the patient to deliver pulses of the laser beam to an interior wall of the patient's heart, further comprising a controller that selects the energy delivered by said pulsed laser beam, and sensing means for providing a first thickness signal indicative of a thickness of the interior wall of the patient's heart, wherein the controller determines the selected energy based upon the thickness signal.

12. The apparatus of claim 11, wherein the laser system comprises:

a flash-pumped laser, including a laser rod and a flash lamp arranged in proximity to the laser rod for causing the laser rod to lase when the flash lamp is turned on;

a capacitor storing energy;

a switchable device connected in series with the capacitor and the flash lamp, the switchable device being responsive to a close circuit control signal to switch from a normally open circuit configuration to a closed circuit configuration to turn on the flash lamp, and being responsive to an open circuit control signal to switch, when a current is passing through the switchable device, from the closed circuit configuration to the open circuit configuration to turn off the flash lamp; and said controller producing the close circuit and open circuit control signals to create the series of micropulses.

* * * * *